(12) United States Patent
Zhong et al.

(10) Patent No.: US 10,149,755 B2
(45) Date of Patent: Dec. 11, 2018

(54) METHOD FOR PREPARING AN ARTIFICIAL HEART VALVE LEAFLET

(71) Applicant: KINGSTRONBIO (CHANGSHU) CO., LTD., Changshu, Jiangsu (CN)

(72) Inventors: Shengping Sam Zhong, Jiangsu (CN); Chang Jin, Jiangsu (CN); Jing Liu, Jiangsu (CN)

(73) Assignee: KINGSTRONBIO (CHANGSHU) CO., LTD., Jiangsu (CN)

( * ) Notice: Subject to any disclaimer, the term of this patent is extended or adjusted under 35 U.S.C. 154(b) by 0 days.

(21) Appl. No.: 15/197,676

(22) Filed: Jun. 29, 2016

(65) Prior Publication Data

US 2016/0310266 A1     Oct. 27, 2016

Related U.S. Application Data

(63) Continuation of application No. PCT/CN2014/073977, filed on Mar. 24, 2014.

(30) Foreign Application Priority Data

Dec. 31, 2013 (CN) .......................... 2013 1 0752640

(51) Int. Cl.
  *A61F 2/24* (2006.01)
  *A61L 27/36* (2006.01)
  *A61L 27/50* (2006.01)

(52) U.S. Cl.
  CPC .......... *A61F 2/2415* (2013.01); *A61L 27/367* (2013.01); *A61L 27/3687* (2013.01); *A61L 27/3691* (2013.01); *A61L 27/507* (2013.01); *A61F 2240/004* (2013.01); *A61L 2430/20* (2013.01)

(58) Field of Classification Search
  None
  See application file for complete search history.

(56) References Cited

U.S. PATENT DOCUMENTS 4,890,457 A * 1/1990 McNally .................. A01N 1/02
                                                          128/DIG. 27
5,613,982 A * 3/1997 Goldstein ........... A61L 27/3604
                                                          424/423
(Continued)

FOREIGN PATENT DOCUMENTS

CN        1107742 A     9/1995
CN        1209048 A     2/1999
(Continued)

OTHER PUBLICATIONS

Armiger et al. Thorax 1985;40:778-786.*
(Continued)

*Primary Examiner* — Julie Wu
*Assistant Examiner* — Douglas F White
(74) *Attorney, Agent, or Firm* — J.C. Patents

(57) ABSTRACT

The present invention provides a method for preparing an artificial heart valve leaflet, comprising freezing an animal tissue membrane and processing the frozen animal tissue membrane so as to reach a preset thickness. The method, by processing the frozen animal tissue membrane, can conveniently obtain an artificial heart valve leaflet with a required thickness and increase the yield of the animal tissue membrane valve leaflet.

10 Claims, 3 Drawing Sheets

(56) References Cited

U.S. PATENT DOCUMENTS

| | | | |
|---|---|---|---|
| 6,378,221 B1 | 4/2002 | Ekholm, Jr. et al. | 33/551 |
| 6,383,732 B1* | 5/2002 | Stone | A01N 1/00 435/1.1 |
| 7,141,064 B2 | 11/2006 | Scott et al. | 623/2.13 |
| 8,846,390 B2* | 9/2014 | Dove | A61F 2/2415 435/325 |
| 2002/0094573 A1 | 7/2002 | Bell | 435/398 |
| 2003/0212454 A1 | 11/2003 | Scott et al. | 623/2.14 |
| 2006/0241744 A1* | 10/2006 | Beith | A61F 2/2415 623/2.17 |
| 2011/0238167 A1* | 9/2011 | Dove | A61F 2/2415 623/2.13 |
| 2013/0110097 A1 | 5/2013 | Schneider et al. | 606/14 |
| 2013/0116676 A1 | 5/2013 | Tian et al. | 606/14 |
| 2013/0310929 A1 | 11/2013 | Dove et al. | 623/2.13 |
| 2014/0257472 A1* | 9/2014 | Kutty | A61F 2/2415 623/2.13 |

FOREIGN PATENT DOCUMENTS

| | | |
|---|---|---|
| CN | 1879578 A | 12/2006 |
| CN | 1961846 A | 5/2007 |
| CN | 101044388 A | 9/2007 |
| CN | 101128225 A | 2/2008 |
| CN | 201040047 Y | 3/2008 |
| CN | 101366975 A | 2/2009 |
| CN | 102293685 A | 12/2011 |
| CN | 102753118 A | 10/2012 |
| CN | 102811681 A | 12/2012 |
| CN | 102899284 A | 1/2013 |
| CN | 103239301 A | 8/2013 |
| WO | WO 02/053069 A2 | 7/2002 |
| WO | WO 2006/129673 A1 | 12/2006 |
| WO | WO 2014/137805 A1 | 9/2014 |

OTHER PUBLICATIONS

International Search Report of corresponding International PCT Application No. PCT/CN2014/073977, dated Oct. 9, 2014.
Chinese First Examination Report of corresponding China patent Application No. 201310752640.3, dated Apr. 28, 2015.
Chinese First Examination Report of corresponding China patent Application No. 201310752640.3, dated Dec. 1, 2015.
The extended European Search Report of corresponding European patent application No. 14877472.2-1462/3090704, dated Sep. 18, 2017.

* cited by examiner

METHOD FOR PREPARING AN ARTIFICIAL HEART VALVE LEAFLET

CROSS-REFERENCE TO RELATED APPLICATIONS

This application is a continuation of International Application No. PCT/CN2014/073977, filed on Mar. 24, 2014, which claims the priority benefit of China Patent Application No. 201310752640.3, filed on Dec. 31, 2013. The contents of the above identified applications are incorporated herein by reference in their entireties.

TECHNICAL FIELD

The present invention relates to a method for preparing an artificial heart valve leaflet, which belongs to the technical field of medical appliance.

BACKGROUND

Heart valve disease is one of the main types of the current heart diseases, which can lead to major heart dysfunction and eventually requires the replacement of native heart valve with artificial heart valve. Bioprosthetic valve is a type of currently used artificial heart valve. Leaflets of the bioprosthetic valve are normally manufactured with an animal tissue membrane, such as pig artery valve or bovine pericardium, and then are sutured to the valve frame of the artificial heart valve after cross-linking and anti-calcification treatment.

In order to meet the function of the valve, each valve leaflet needs to meet particular requirements, for example, under some situation, different valve leaflets of one valve need to keep an identical thickness. For the surgically implanted bioprosthetic valve, according to the difference of the valve sizes, the required thicknesses of the valve leaflets are normally in the range of 0.3-0.6 mm. However, currently the thicknesses of the bovine pericardium collected from the slaughter houses are usually in the range of 0.1-0.8 mm and points of each piece of the bovine pericardium have different thicknesses. Therefore, usually only 1-2 pieces of qualified valve leaflets can be obtained from each piece of the pericardium, which results in a low yield. As for the transcatheter heart valve, in order to increase the transportability via blood vessels, the pre-installing diameter of the heart valve need to be reduced, which requires an even thin animal tissue membrane with thickness normally lower than 0.25 mm. Therefore, very few animal tissue membranes can be used for transcatheter heart valve, which leads to even lower yield.

Under other circumstances, in order to satisfy particular functions, it requires that points of the artificial valve leaflets have different thicknesses, which is difficult to be met by using the above mentioned method.

Therefore, the animal tissue membrane needs to be processed to meet the requirement for the thickness of the valve leaflets. U.S. Pat. No. 7,141,064 discloses a method for obtaining an animal tissue membrane with relatively uniform or relatively thin thickness by pressing during cross-linking treatment, the method can increase productivity. However, this method may be likely to straighten the corrugated fibers of the animal tissue membrane (such as bovine pericardium) and reduce its elasticity, and thereby affect bend and stretch effects of the valve leaflets during heart dilation and contraction, and also it is difficult to obtain valve leaflets with different thicknesses at different positions. Patent US2013110097, US20130116676 and US20130310929 disclose methods of processing a tissue in a state of crosslinking or semi-crosslinking by laser removal, scraping, grinding, etc. so as to make the thicknesses of the tissues uniform or reduced and to obtain a valve leaflet structure with different thicknesses at different spots. However, the animal tissue membrane used for the artificial heart valve is often a soft tissue, and when processing using the methods described above, the soft tissue tends to become deformed and corrugated, is hard to manipulate, and it is difficult to remove the residual debris of the tissue after processing.

SUMMARY

The present invention provides a method for preparing an artificial heart valve leaflet by freezing an animal tissue membrane before processing. The method can conveniently obtain an artificial heart valve leaflet with a required thickness, increase the yield of the valve leaflet from the animal tissue membrane, and reserve the intrinsic elastic fiber layer of the animal tissue membrane.

The present invention provides a method for preparing an artificial heart valve leaflet, including freezing an animal tissue membrane, and processing the frozen animal tissue membrane to a preset thickness. Those skilled in the art will understand that if the animal tissue membrane is frozen while unfolded or tiled, it is more beneficial to the processing.

Further, liquid nitrogen is used to freeze the animal tissue membrane.

Further, the animal tissue membrane is immersed in the liquid nitrogen for processing.

Further, the processing includes one or more of grinding, cutting, scraping, milling and ablation.

Further, prior to freezing the animal tissue membrane, or after processing the frozen animal tissue membrane to the preset thickness, the method further includes processing the animal tissue membrane to a required shape of the artificial heart valve leaflet.

Further, the animal tissue membrane is placed on a mould having a thickness distribution corresponding to that of the artificial heart valve leaflet, and then is frozen.

Further, prior to freezing the animal tissue membrane, the method further includes using a cryoprotectant to pre-treat the animal tissue membrane.

Further, the step of processing the frozen animal tissue membrane to a preset thickness is to reduce entire thickness of the animal tissue membrane to a preset thickness, or to process different portions of the animal tissue membrane to respective thicknesses as required.

Further, the processing is to place the animal tissue membrane into a concave die with a depth equal to the preset thickness for processing, so as to reduce the entire thickness of the animal tissue membrane to the preset thickness.

Further, the animal tissue membrane is pericardium, diaphragm or endocranium of a mammal.

Further, the processing is conducted on a fibrous surface of the animal tissue membrane.

Further, the animal tissue membrane is processed with cross-linking treatment.

The embodiments of the present invention at least have the following advantages:

1. The method of the present invention can obtain an artificial heart valve leaflet with a required thickness and also can easily fix and process the animal tissue membrane, which reduces damages to the animal tissue membrane and increases the accuracy of the thickness of the artificial heart valve leaflet.

2. The method of the present invention can improve the yield of the artificial heart valve leaflet which in turn reduces the cost of the raw material.

3. The method of the present invention can reserve elasticity function of the corrugated fiber layer of the animal tissue membrane (such as pericardium of a mammal), and guarantee the bend and stretch effect of the artificial heart valve leaflet during heart dilation and contraction.

DESCRIPTION OF EMBODIMENTS

Figure 1:
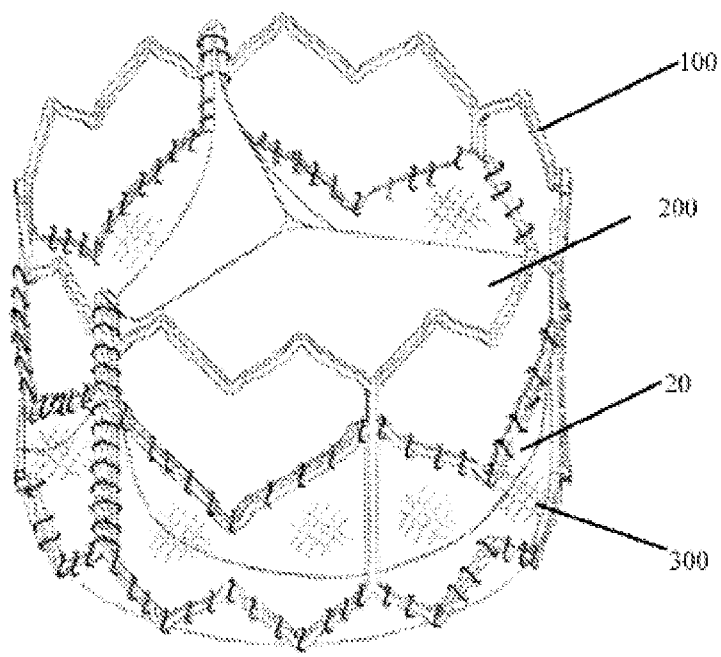
FIG. 1 shows a structure diagram of a transcatheter artificial heart valve.
Figure 2:
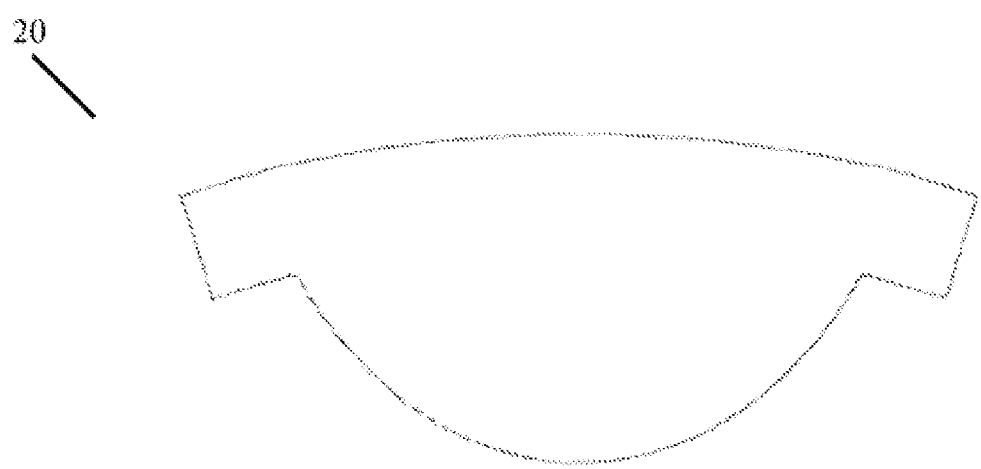
FIG. 2 shows a valve leaflet that is prepared according to an embodiment of the present invention and may be used in the transcatheter artificial heart valve shown in FIG. 1.

The present invention will be described in detail with reference to the embodiments together with the figures. However, the present invention can be implemented in different forms and should not be limited to the presented embodiments.

The present invention provides a method for preparing an artificial heart valve leaflet by freezing an animal tissue membrane before processing; the method can conveniently obtain an artificial heart valve leaflet with a required thickness, increase the yield of the valve leaflet from the animal tissue membrane, and reserve the intrinsic elasticity of the animal tissue membrane.

The Pre-Treatment Prior to Freezing:

Because the animal tissue membrane contains a certain amount of water, it usually needs to pre-treat the animal tissue membrane prior to the freezing, which is more favorable maintain structural integrity of the animal tissue membrane. The pre-treatment prior to freezing can be conducted directly on the entire animal tissue membrane, or on the animal tissue membrane that has been tailored to the shape of the valve leaflet. The pre-treatment prior to freezing is immersing the animal tissue membrane in a cryoprotectant for processing. The cryoprotectant may be glycerin, dimethyl sulfoxide, ethylene glycol or propylene glycol, etc.

Freezing:

After the pre-treatment prior to freezing, the animal tissue membrane is placed in a refrigerating apparatus (e.g. liquid nitrogen tank or other container) for freezing until the animal tissue membrane will not deform during processing and thereby is capable of being processed. In order to be more beneficial to the processing, the animal tissue membrane is frozen when unfolded or tiled. The animal tissue membrane can also be placed, before freezing, in a mould having a thickness distribution corresponding to that of the artificial heart valve leaflet; for example, a mould having such a structure that the center thereof is convex and the periphery is concave in relative to the center may be used, the animal tissue membrane is attached to the mould during freezing, and in subsequent processing, the surface of the animal tissue membrane that is not attached to the mould is processed into a flat surface, which allows the animal tissue membrane has a relatively small thickness in the area where the animal tissue membrane is attached to the convex center of the mould and has a relatively large thickness in the area where the animal tissue membrane is attached to the concave periphery of the mould, and then a valve leaflet with a corresponding thickness distribution can be prepared.

Commercial liquid nitrogen can be used in the present invention, and the liquid nitrogen normally has a temperature of around −196° C., and can achieve rapid freezing.

Processing:

After the animal tissue membrane is frozen, the processing is conducted on a surface of the frozen animal tissue membrane. An area that needs to be tailored to a valve leaflet is determined first on the animal tissue membrane, and when portions of the valve leaflet have the same thickness actually required (i.e., the preset thickness), the processing is to reduce the thickness of the relatively thick area of the animal tissue membrane in the determined area so that the determined area has a uniform thickness; further, if the preset thickness of the valve leaflet is smaller than the uniform thickness obtained above, further reprocessing can be conducted to further reduce the thickness of the entire animal tissue membrane until the preset thickness is arrived. When areas of the valve leaflet have different preset thicknesses, the processing can be conducted on respective areas according to their preset thicknesses. Or, the processing can be conducted until the entire animal tissue membrane reaches a thickness that is relatively larger than the preset thicknesses of respective areas thereof, and then an area that needs to be tailored to a valve leaflet is determined on the animal tissue membrane and the animal tissue membrane in the area is processed to a thickness as required.

After completion of the above processing, the animal tissue membrane can be tailored to a required valve leaflet shape by for example mechanical cutting in frozen state, or tailored to a required valve leaflet shape by for example a mechanical or laser method after unfreezing.

Or, the animal tissue membrane is tailored to a required valve leaflet shape by a conventional method before freezing and then is frozen, after that, the processing can be conducted in the frozen state according to needs, to reduce the thickness of a relatively thick area of the animal tissue membrane to reach a uniform entire thickness; further, for a valve leaflet that have the smaller preset thickness, it can be further processed to further reduce the entire thickness of the animal tissue membrane so that the thickness accords with the smaller preset thickness, or process can be conducted on respective areas according to their preset thickness.

The processing above conducted in the frozen state can select from grinding, cutting, scraping, milling, ablation and other methods that can partially or entirely reduce the tissue membrane thickness; the methods mentioned above can also be used in combination. For example, an animal tissue membrane is fixed in a fixture and put in liquid nitrogen to get frozen, and then the frozen animal tissue membrane with the fixture is processed; of course, the animal tissue membrane can also be fixed after freezing and then is processed. The animal tissue membrane can be processed by fixing it on the grinding (e.g. grinder), milling (e.g. miller) or cutting (e.g. planer) device, or by the manual grinding tool, ablation tool or scraper, etc.

The animal tissue membrane used in the present invention is any animal tissue membrane that can be used for an artificial heart valve leaflet, such as the pericardium (or pericardial patch) of mammals such as bovine, horse, etc. The animal tissue membrane usually has a fibrous surface and a relatively smooth surface, the fibrous surface is usually in contact with other tissues in the animal, whereas the smooth surface is usually close to the tissues that are covered by the animal tissue membrane, and usually is a corrugated elastic fiber layer formed by collagen protein, etc. In specific embodiments, the fibrous surface of the animal tissue membrane may be selected to be processed, which is favorable to reserve the elastic fiber layer and can make the fibrous surface flat and smooth.

Under some circumstances, different areas of the valve leaflet may have different thicknesses, which is convenient for the valve leaflet to connect with and be fixed to a fixture, can improve the durability of the valve leaflet or can support the valve leaflet to prevent collapse, etc. In the present invention, processing can be conducted on the animal tissue membrane according to the requirements mentioned above. For example, a relatively large thickness can be remained for the connection area between the valve leaflets and valve frame; or by simulating the thickness distribution and mechanical characteristics of human physiological valve, the animal tissue membrane is processed to reach a thickness distribution that is the same as or similar to the thickness distribution of the human physiological valve.

In the present invention, for the processing conducted in the frozen state, the tissue or valve leaflet that needs to be processed can be immersed in liquid nitrogen directly or by fixing via a fixture; or the tissue or valve leaflet after freezing may be placed into or onto a surface of the liquid nitrogen refrigerating device, which is in favor of maintaining the frozen state and is easy to process and operate.

In the present invention, when portions of the animal tissue membrane have the same preset thickness as required, the animal tissue membrane may be placed in a concave die when processing, where the concave die has a groove with a required thickness and shape, and the depth of the groove corresponds to the required preset thickness. A processing tool (such as manual scraper or ablation tool) having a working surface larger than the width of the concave die is used for processing, and the processing tool can move along an outer surface of the concave die by position limit via a surface of the concave die, to obtain the animal tissue membrane with uniform thickness. Using the concave die for processing is more easy to operate, and is beneficial to obtain the animal tissue membrane with more uniform thickness.

The following description explains the embodiments of the present invention in combination with the figures.

Embodiment 1

The present invention provides a method for preparing an artificial heart valve leaflet. FIG. 1 shows a structure diagram of a transcatheter 1 artificial valve. The valve includes a cylindrical stent 100, a valve leaflet 200 having 3 valve leaflets and a skirt 300. The valve leaflet 200 is set inside the cylindrical stent 100, where each of the valve leaflets has a shape as shown in figure, and is fixed to the cylindrical stent 100 via the suture line. The skirt 300 is arranged, along its circumferential direction, between the cylindrical stent 100 and the valve leaflet 200.

Figure 4:
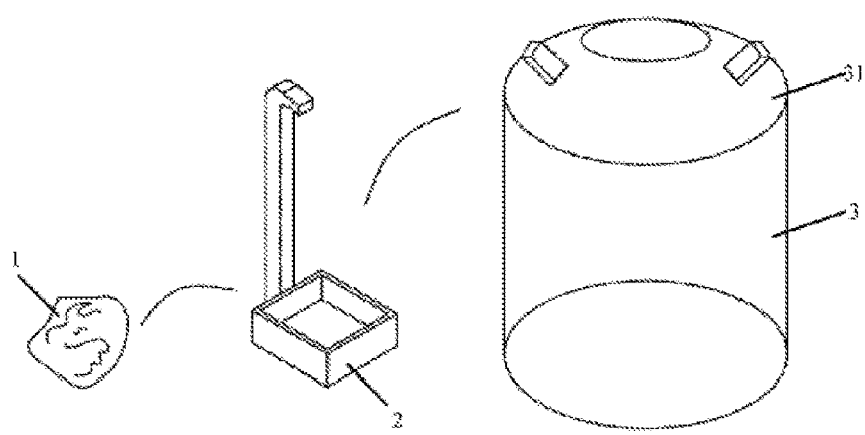
FIG. 4 shows a flow chart of a method for preparing an artificial heart valve leaflet according to the present invention.

The preparation procedure of the valve leaflet 20 is shown in FIG. 4. A bovine pericardial patch 1 (whose thickness is in the range of 0.3-0.8 mm) is collected to fabrication the valve leaflet, and is pre-treated prior to freezing, and then is put into a basket 2, where the pericardial patch 1 may be processed with cross-linking treatment, which is beneficial to improving the stability of tissues of the pericardial patch. Then the basket 2 is put into a liquid nitrogen tank 3 for freezing. The frozen pericardial patch 1 is then taken out from the liquid nitrogen tank 3 and the basket 2, and is fixed to a surface of a liquid nitrogen refrigerating device 31, and since the surface is a datum plane for measuring thickness during processing, the surface should be flat. The smooth surface of the pericardial patch 1 faces down when fixing.

Figure 5:
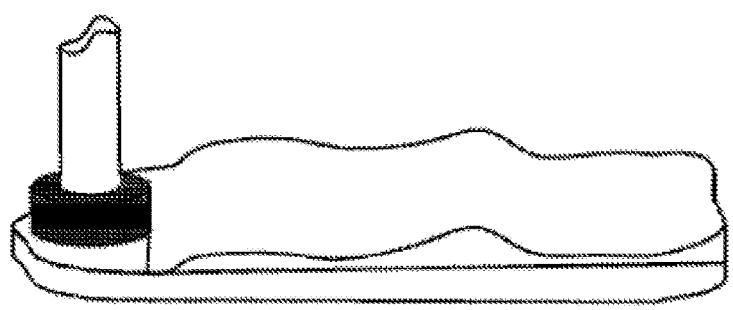
FIG. 5 shows a diagram of a method for preparing an artificial heart valve leaflet according to an embodiment of the present invention.

As shown in FIG. 5, the grinding method may be used to grind the fibrous surface of the fixed pericardial patch 1 until the thickness of the pericardial patch 1 reaches 0.25 mm and is uniform. Then the grinded pericardial patch 1 is taken off for cleaning to remove fragments and residuals after grinding. Then defrosting is conducted, and a suitable area is selected according to the size of the valve leaflet and then is processed to a required shape and eventually a valve leaflet 20 is obtained.

Embodiment 2

The present embodiment provides a method for preparing an artificial heart valve leaflet that can be used for the transcatheter valve described in Embodiment 1 and can also be used for other bioprosthetic valves that use an animal pericardium as a valve leaflet.

Figure 6:
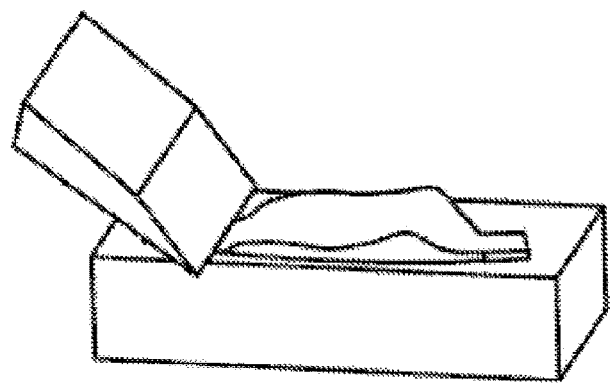
FIG. 6 shows a diagram of a method for preparing an artificial heart valve leaflet according to another embodiment of the present invention.

The preparation for the valve leaflet 20 is as shown in FIG. 4, which includes cutting a bovine pericardial patch to the shape of a valve leaflet; selecting the pericardial patch 1 having the valve leaflet, with each portion of the pericardial patch having a thickness larger than the required preset thickness, and pre-treating the pericardial patch prior to freezing; then placing the pericardial patch 1 having the valve leaflet shape into a concave die shown in FIG. 6 with the smooth surface of the pericardial patch 1 facing down, where the concave die has a groove that has the same shape as that of the valve leaflet and that has a depth equal to the preset thickness of the valve leaflet; then placing the pericardial patch 1 together with the concave die into the basket 2 and placing the basket 2 into the liquid nitrogen tank 3 for freezing. Then the frozen concave die is taken out together with the pericardial patch 1 and fixed onto the surface 31 of the liquid nitrogen refrigerating device.

As shown in FIG. 6, the processing may be conducted by scraping, where the scraper has a working surface with a size larger than the width of the groove, the pericardial patch 1 having the valve leaflet shape is scraped layer by layer until the pericardial patch has a thickness equal to the depth of the groove (i.e., the preset thickness of the valve leaflet), then the valve leaflet is obtained. Since the scraper has a relatively large size, the edge of the concave die may play a role in position limit, which is beneficial to eventually controlling the accuracy of the thickness of the valve leaflet and improving the uniformity of the thickness. After processing, the obtained valve leaflet is taken off for cleaning to remove fragments and residuals after grinding and then is unfrozen.

Embodiment 3

Figure 3A:
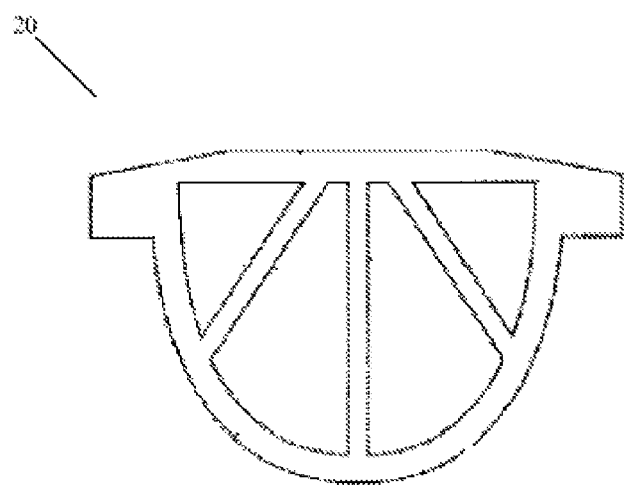
FIGS. 3A and 3B show valve leaflets prepared according to another embodiment of the present invention.
Figure 3B:
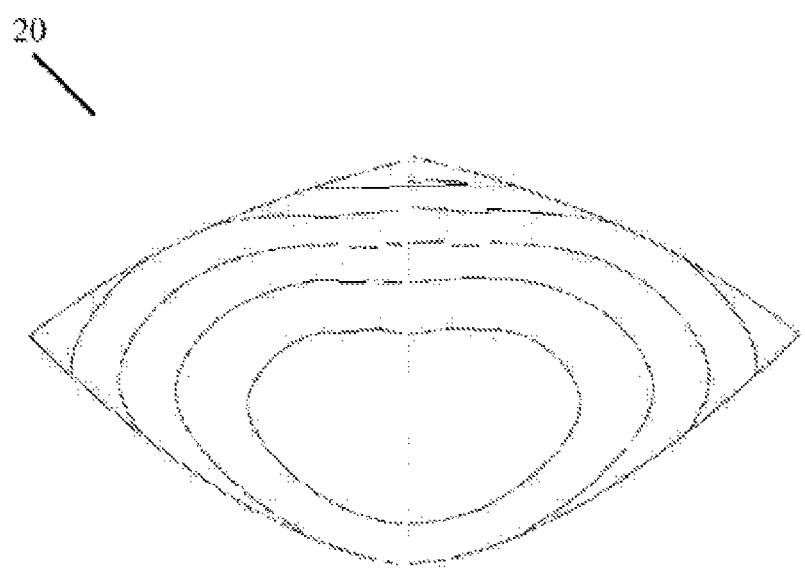

The present embodiment provides a method for preparing a valve leaflet with different thicknesses. The structure of the valve leaflet with different thicknesses may refer to the valve leaflet described in patent US20130116676. As shown in FIG. 3A, the periphery of the valve leaflet is thicker than the center thereof, which is in favor of increasing suture strength to the valve frame. Moreover, the center is arranged with a stiffener for supporting the valve leaflet when the valve leaflet is thin. The valve leaflet can also have a thickness distribution similar to human physiological valve, as shown in FIG. 3B, that is, the center of the valve leaflet is thinner and it is gradually thicker from the center to the periphery.

The preparation of the valve leaflet 20 is as shown in FIG. 4, which includes cutting a bovine pericardial patch to the shape of a valve leaflet; selecting the pericardial patch 1 having the valve leaflet with each portion of the pericardial patch having a thickness larger than the required preset thickness, and pre-treating the pericardial patch prior to freezing; then placing the pericardial patch 1 having the valve leaflet shape into a concave die shown in FIG. 6 with the smooth surface of the pericardial patch 1 facing down, where the concave die has a groove that has the same shape as that of the valve leaflet and that has a depth equal to the preset thickness of the thinnest portion of the valve leaflet; then placing the pericardial patch 1 together with the concave die into the basket 2 and placing the basket 2 into the liquid nitrogen tank 3 for freezing. Then the frozen concave die is taken out together with the pericardial patch 1 and fixed onto the surface 31 of the liquid nitrogen refrigerating device.

The processing may be conducted by scraping, as shown in FIG. 6, or by grinding, as shown in FIG. 5. A small cutting head or grinding head may be used when scraping or grinding, which is beneficial to partially reducing thickness of the valve leaflet. Measurements for portions are made during processing until each portion is processed to corresponding preset thickness and then the valve leaflet 20 is obtained. After processing, the obtained valve leaflet 20 is taken off for cleaning to remove fragments and residuals after scraping or grinding and then is unfrozen.

Finally, it should be noted that the above embodiments are merely provided for describing rather than limiting the technical solutions of the present invention. It should be understood by persons skilled in the art that although the present invention has been described in detail with reference to the foregoing embodiments, modifications can be made to the technical solutions described in the foregoing embodiments, or equivalent replacements can be made to part or all technical features in the technical solutions; however, such modifications or replacements do not cause the essence of corresponding technical solutions to depart from the scope of the embodiments of the present invention.

What is claimed is:

1. A method for preparing an artificial heart valve leaflet comprising
   pre-treating an animal tissue membrane comprised of immersing the animal tissue membrane in a cryoprotectant,
   freezing the animal tissue membrane comprised of placing the animal tissue membrane on a mould having a center that is convex and periphery that is concave relative to the center of said mould, and having a thickness distribution corresponding to that of the artificial heart valve leaflet; and then together with the mould the animal tissue membrane is immersed into liquid nitrogen for freezing, and
   processing the frozen animal tissue membrane to a preset thickness.

2. The method of claim 1, wherein the animal tissue membrane is immersed into the liquid nitrogen for processing.

3. The method of claim 1, wherein the processing comprises one or more of grinding, cutting, scraping, milling and ablation.

4. The method of claim 1, further comprising processing the animal tissue membrane to a required shape of the artificial heart valve leaflet, prior to freezing the animal tissue membrane, or after processing the frozen animal tissue membrane to the preset thickness.

5. The method of claim 1, wherein the processing is conducted on a fibrous surface of the animal tissue membrane.

6. The method of claim 1, wherein the animal tissue membrane is processed with a cross-linking treatment.

7. The method of claim 1, wherein the processing the frozen animal tissue membrane to a preset thickness comprises reducing the entire thickness of the animal tissue membrane to a preset thickness, or processing different portions of the animal tissue membrane to respective thicknesses as required.

8. The method of claim 1, wherein the processing the frozen animal tissue membrane to a preset thickness comprises placing the animal tissue membrane into a concave die with a depth equal to the preset thickness for processing, so as to reduce the entire thickness of the animal tissue membrane to the preset thickness.

9. The method of claim 1, wherein the animal tissue membrane is pericardium, diaphragm or endocranium of a mammal.

10. The method of claim 9, wherein the processing is conducted on a fibrous surface of the animal tissue membrane.

\* \* \* \* \*